| United States Patent [19] | [11] | 4,209,512 |
|---|---|---|
| Tomita et al. | [45] | Jun. 24, 1980 |

[54] MONO- AND DI-THIOPHOSPHATE ESTERS CONTAINING AN ISOXAZOLINONE RING AND COMPOSITIONS AND METHODS CONTAINING THE SAME

[75] Inventors: Kazuo Tomita; Tadashi Murakami, both of Hiromachi; Hideakira Tsuji, Yasu; Keigo Matsumoto, Yasu; Katsuhiro Fujita, Yasu; Shinji Yokoi, Yasu, all of Japan

[73] Assignee: Sankyo Company Limited, Tokyo, Japan

[21] Appl. No.: 911,426

[22] Filed: Jun. 1, 1978

[30] Foreign Application Priority Data

Jun. 9, 1977 [JP] Japan .................................. 52-68325

[51] Int. Cl.$^2$ ..................... A01N 9/36; C07D 261/12; C07F 9/65
[52] U.S. Cl. ................................... 424/200; 548/113; 548/112; 424/357; 548/241; 548/243
[58] Field of Search ................... 424/200; 260/307 A, 260/307 H

[56] References Cited

U.S. PATENT DOCUMENTS

| 3,755,344 | 8/1973 | Lorenz et al. ................. 260/307 A |
| 3,798,230 | 3/1974 | Beutel et al. ................. 260/307 A |
| 3,920,677 | 11/1975 | Meyer et al. ................. 260/307 A |

FOREIGN PATENT DOCUMENTS

| 769084 | 12/1971 | France ................................ 424/200 |
| 713278 | 8/1954 | United Kingdom ............... 260/307 A |

*Primary Examiner*—Dale R. Ore
*Attorney, Agent, or Firm*—Frishauf, Holtz, Goodman & Woodward

[57] ABSTRACT

Mono- and di-thiophosphate esters having an isoxazolinone system attached at its 2-position through an optionally alkyl- or phenyl-substituted methylene or ethylene group to the sulphur or to one of the sulphur atoms are useful as insecticides and/or acaricides.

19 Claims, No Drawings

MONO- AND DI-THIOPHOSPHATE ESTERS CONTAINING AN ISOXAZOLINONE RING AND COMPOSITIONS AND METHODS CONTAINING THE SAME

BACKGROUND OF THE INVENTION

The present invention provides a novel series of mono- and di-thiophosphate esters containing an isoxazolinone system, which have valuable insecticidal and acaricidal properties; the invention also provides insecticidal and/or acaricidal compositions containing the novel compounds of the invention and a process for preparing these compounds.

Insects and arachnids cause considerable damage to plants, both agricultural and domestic, can be a serious danger to health or, as best, are a considerable nuisance. Accordingly, considerable sums are spent on their destruction. Although many insecticides and acaricides are available, many of them have to be used with considerable care because they endanger the health of humans or other animals or because of their phytotoxicity. Moreover, because of their short life cycles, insects and arachnids can develop immunity to many of the commonly used insecticides and acaricides and, accordingly, there is always a continuing need for new compounds exhibiting insecticidal and/or acaricidal properties.

BRIEF SUMMARY OF THE INVENTION

It is, therefore, an object of the present invention to provide novel mono- and di-thiophosphate esters having insecticidal and/or acaricidal properties.

It is a further object of the invention to provide a process for producing these novel mono- and di-thiophosphate esters.

It is a still further object of the invention to provide insecticidal and/or acaricidal compositions containing the mono- and di-thiophosphate esters.

The compounds of the invention have the formula (I):

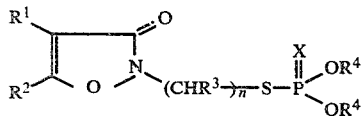

in which:
$R^1$ represents a hydrogen atom, a lower alkyl group or a halogen atom;
$R^2$ represents a hydrogen atom, a lower alkyl group or a phenyl group;
$R^3$ represents a hydrogen atom, a lower alkyl group or a phenyl group.
$R^4$ represents a lower alkyl group;
X represents an oxygen atom or a sulphur atom; and
n represents 1 or 2 and, when n represents 2, the groups $R^3$ can be the same or different.

The invention also provides an insecticidal and/or acaricidal composition which contains at least one compound of formula (I) as the active ingredient.

In the above, the term "lower alkyl" preferably means an alkyl group having from 1 to 4 carbon atoms.

DETAILED DESCRIPTION OF INVENTION

In the compounds of formula (I) when $R^1$ represents a lower alkyl group, it may be, for example, a methyl, ethyl, n-propyl, isopropyl or n-butyl group. When $R^1$ represents a halogen atom, it may be a chlorine, bromine, iodine or fluorine atom.

When $R^2$, $R^3$ and $R^4$, which may be the same or different, are lower alkyl groups, they may be, for example, methyl, ethyl, n-propyl, isopropyl or n-butyl groups.

A preferred class of compounds of formula (I) are those in which: $R^1$ represents a hydrogen atom, a methyl group or a halogen atom; $R^2$ represents a hydrogen atom, a lower alkyl group or a phenyl group; $R^3$ represents a hydrogen atom or a methyl group; $R^4$ represents a lower alkyl group; X represents a sulphur atom and n is 1.

The following is a non-limiting list containing examples of compounds of formula (I), except for Nos. 9 and 14 which are outside the scope of this invention. The numbers appended to the compounds in this list will be used to identify them in the following Examples.

1. O,O-diethyl S-(5-methyl-3-oxo-4-isoxazolin-2-ylmethyl)phosphorodithioate.
2. O,O-diethyl S-(5-methyl-3-oxo-4-isoxazolin-2-ylethyl)phosphorothioate.
3. O,O-diethyl S-(4-chloro-5-methyl-3-oxo-4-isoxazolin-2-ylmethyl) phosphorodithioate.
4. O,O-diethyl S-(4-chloro-5-methyl-3-oxo-4-isoxazolin-2-ylmethyl) phosphorothioate.
5. O,O-diethyl S-(4-chloro-3-oxo-5-phenyl-4-isoxazolin-2-ylmethyl) phosphorodithioate.
6. O,O-diethyl S-(3-oxo-5-phenyl-4-isoxazolin-2-ylmethyl) phosphorodithioate.
7. O,O-dimethyl S-(5-methyl-3-oxo-4-isoxazolin-2-ylmethyl) phosphorodithioate.
8. O,O-diethyl S-(3-oxo-4-isoxazolin-2-ylmethyl) phosphorodithioate.
9. O,O-diethyl S-(3-oxobenzisoxazolin-2-ylmethyl) phosphorodithioate.
10. O,O-diethyl S-[2-(5-methyl-3-oxo-4-isoxazolin-2-yl)ethyl] phosphorodithioate.
11. O,O-diethyl S-[1-(5-methyl-3-oxo-4-isoxazolin-2-yl)ethyl] phosphorodithioate.
12. O,O-dimethyl S-[1-(5-methyl-3-oxo-4-isoxazolin-2-yl)ethyl] phosphorodithioate.
13. O,O-diethyl S-[1-(5-methyl-3-oxo-4-isoxazolin-2-yl)ethyl] phosphorothioate.
14. O,O-dimethyl S-(3-oxobenzisoxazolin-2-ylmethyl) phosphorodithioate.
15. O,O-diethyl S-[α-(5-methyl-3-oxo-4-isoxazolin-2-yl)benzyl] phosphorodithioate.
16. O,O-dimethyl S-(4-chloro-5-methyl-3-oxo-4-isoxazolin-2-ylmethyl) phosphorodithioate.
17. O,O-diisopropyl S-(4-chloro-5-methyl-3-oxo-4-isoxazolin-2-ylmethyl) phosphorodithioate.
18. O,O-dimethyl S-(4-chloro-3-oxo-5-phenyl-4-isoxazolin-2-ylmethyl) phosphorodithioate.
19. O,O-di-n-propyl S-(4-chloro-3-oxo-5-phenyl-4-isoxazolin-2-ylmethyl) phosphorodithioate.
20. O,O-diisopropyl S-(4-chloro-3-oxo-5-phenyl-4-ioxazolin-2-ylmethyl) phosphorodithioate.
21. O,O-dimethyl S-(3-oxo-5-phenyl-4-isoxazolin-2-ylmethyl) phosphorodithioate.
22. O,O-di-n-propyl S-(3-oxo-5-phenyl-4-isoxazolin-2-ylmethyl) phosphorodithioate.

23. O,O-diisopropyl S-(3-oxo-5-phenyl-4-isoxazolin-2-ylmethyl) phosphorodithioate.
24. O,O-di-n-propyl S-(5-methyl-3-oxo-4-isoxazolin-2-ylmethyl) phosphorodithioate.
25. O,O-diisopropyl S-(5-methyl-3-oxo-4-isoxazolin-2-ylmethyl) phosphorodithioate.
26. O,O-di-n-propyl S-(4-chloro-5-methyl-3-oxo-4-isoxazolin-2-ylmethyl) phosphorodithioate.
27. O,O-dimethyl S-(4-bromo-5-methyl-3-oxo-4-isoxazolin-2-ylmethyl) phosphorodithioate.
28. O,O-diisopropyl S-(4-bromo-5-methyl-3-oxo-4-isoxazolin-2-ylmethyl) phosphorodithioate.
29. O,O-dimethyl S-(4-bromo-5-methyl-3-oxo-4-isoxazolin-2-ylmethyl) phosphorodithioate.
30. O,O-diethyl S-(3-oxo-5-n-propyl-4-isoxazolin-2-ylmethyl) phosphorodithioate.
31. O,O-diethyl S-(4,5-dimethyl-3-oxo-4-isoxazolin-2-ylmethyl) phosphorodithioate.
32. O,O-diisopropyl S-(4,5-dimethyl-3-oxo-4-isoxazolin-2-ylmethyl) phosphorodithioate.
33. O,O-diethyl S-[α-(4-chloro-5-methyl-3-oxo-4-isoxazolin-2-yl)benzyl] phosphorothioate.
34. O,O-diethyl S-[α-(3-oxo-5-phenyl-4-isoxazolin-2-yl)benzyl] phosphorodithioate.
35. O,O-diethyl S-(4-isopropyl-3-oxo-5-phenyl-4-isoxazolin-2-ylmethyl) phosphorodithioate.
36. O,O-di-n-propyl S-(4-isopropyl-3-oxo-5-phenyl-4-isoxazolin-2-ylmethyl) phosphorodithioate.

The novel compounds of formula (I) may be prepared by reacting an isoxazolinone derivative of formula (II):

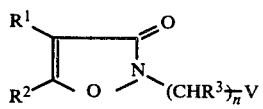

(in which Y represents a halogen atom, and $R^1$, $R^2$, $R^3$ and n are as defined above) with a salt of a phosphate ester of general formula (III)

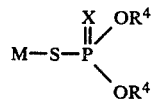

(in which $R^4$ and X are as defined above, and M represents an alkali metal atom, an ammonium ion or an organic ammonium ion).

The reaction is preferably carried out by dissolving the isoxazolinone derivative of formula (II) in a solvent and then adding the salt (III) as such or dissolving or dispersing it in a solvent and adding the solution or dispersion, and finally stirring the resulting mixture at the reaction temperature. There is no particular limitation upon the nature of the solvent employed, provided that it has no adverse effect upon the reaction. Suitable solvents include: aromatic hydrocarbons, such as benzene; chlorinated aliphatic hydrocarbons, such as methylene chloride; and ketones, such as methyl ethyl ketone or acetone. A single such solvent or a mixture of two or more thereof may be employed. Of these solvents, we prefer to use acetone. The order of addition of the reactants is in no way critical and, if desired, instead of adding the salt (III) to the isoxazolinone derivative (II), the isoxazolinone derivative (II) may be added to the salt (III).

There is also no particular limitation on the reaction temperature and, for this reason, it is preferable to use ambient temperature, although temperatures above or below this may be employed, if desired.

After completion of the reaction, the desired product may be separated from the reaction mixture by conventional means. For example, if the reaction is performed in a water-miscible solvent, such as acetone, the solvent is distilled off; water and a water-immiscible solvent (such as benzene, diethyl ether or methylene chloride) are added to the residue; the aqueous phase is separated; the organic phase is washed, e.g. with, in turn, an aqueous solution of an alkali metal carbonate and water; the solution is dried; and finally the solvent is distilled off, affording the desired compound. This compound may, if necessary, be further purified using any appropriate conventional technique, such as chromatography.

The isoxazolinone derivatives of formula (II) used as intermediates in the synthesis of the compounds of formula (I) are also novel compounds and form part of the invention. The preparation of these novel intermediates is given below.

Compounds of formula (II) in which n is 1 may be prepared by reacting a compound of formula (IV):

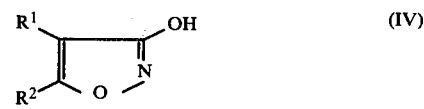

(in which $R^1$ and $R^2$ are as defined above) with a compound of formula (V):

(in which $R^3$ is as defined above) or a polymer thereof and with a compound of formula (VI):

(in which Y is as defined above and the two groups Y may be the same or different).

The aldehyde of formula (V) or its polymer employed will depend upon the compound of formula (II) which it is desired to produce. Examples of such aldehydes and their polymers include: formaldehyde, trioxymethylene, paraformaldehyde, acetaldehyde, paraldehyde and benzaldehyde. Examples of suitable thionyl halides of formula (VI) include thionyl chloride, thionyl bromide, thionyl fluoride and thionyl bromochloride, of which we prefer thionyl chloride and thionyl bromide.

Although we do not wish to be limited on any theory, it is believed that, in the above reaction, the isoxazole of formula (IV) reacts first with the aldehyde of formula (V) to give a compound of formula (VII):

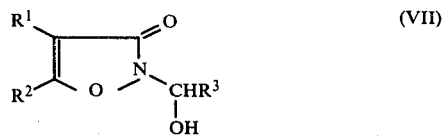

(in which $R^1$, $R^2$ and $R^3$ are as defined above). After this, compound (VII) reacts with the thionyl halide of formula (VI) to give the desired compound of formula (II).

Thus, one way of carrying out the reaction to prepare the intermediate of formula (II) is to react the compound of formula (IV) first with the aldehyde of formula (V), or its polymer preferably in equimolar amounts or with the aldehyde in a slight excess. This gives the compound of formula (VII), which, with or without intermediate isolation, is then reacted with the thionyl halide of formula (VI), the thionyl halide preferably being employed in an amount greater than equimolar, thus affording the desired compound of formula (II). Although the intermediate compound of formula (VII) can be isolated, if desired, it is generally somewhat unstable and we therefore prefer that it should not be isolated.

An alternative way of preparing the intermediate isoxazolinone derivatives of formula (II) is to react the isoxazole of formula (IV) with a mixture of the aldehyde (V) or polymer and the thionyl halide (VI). The aldehyde is preferably employed in an equimolar amount or in a slight excess and the thionyl halide is preferably employed in an amount in excess of equimolar.

It will, therefore, be understood that the order of addition of compounds (IV), (V), and (VI) is not critical in the preparation of the compounds of formula (II). The reaction is preferably carried out in the presence of an inert organic solvent; where a solvent is employed, its nature is not critical, provided that it has no adverse effect upon the reaction. Examples of suitable solvents include: halogenated hydrocarbons, such as methylene chloride and chloroform; and aromatic hydrocarbons, such as benzene, toluene and xylene. The reaction may be carried out over a wide range of temperatures, but is preferably carried out at a temperature from 0° C. to the reflux temperature of the solvent employed and is more preferably carried out at a temperature within the range from 10° C. to 80° C. The reaction is complete when evolution of hydrogen halide and sulphur dioxide gas ceases.

After completion of the reaction, the compound of formula (II) can be obtained by evaporating the solvent and the excess thionyl halide (if any) from the reaction mixture. If necessary, the compound may be purified by conventional means, e.g. by recrystallization or by column chromatography, which can be performed under conditions known per se.

Compounds of formula (II) in which n is 2, may be obtained by reacting a compound of formula (IV), defined above, with a compound of formula (VIII):

(VIII)

(in which Y is as defined above). The simplest means of carrying out this reaction is merely to heat together a mixture of the two reactants under reflux.

We have found that the compounds of formula (I) exhibit insecticidal and/or acaricidal activity against a wide variety of insect and arachnid pests, including agricultural insects and mites, such as rice stem borers, planthoppers, rice leafhoppers, scale insects, leaf rollers, mites and aphids, as well as domestic insects, such as flies, mosquitoes and cockroaches.

In order to control effectively harmful insects, arachnids and acarids, the compounds of formula (I) may be formulated with carriers and diluents well-known in this art, particularly with agriculturally-acceptable carriers and diluents, by conventional techniques. The resulting compositions may be in various forms, including liquids, dusts, granules and wettable powders.

Liquid formulations may be prepared by dissolving the active compound of formula (I) in an appropriate liquid and, if desired, adding conventional adjuvants, such as emulsifying or dispersing agents. Suitable solvents include alcohols, such as methanol and ethanol; ketones, such as acetone; aromatic hydrocarbons, such as benzene and xylene; and other conventional solvents, such as solvent naphtha. Examples of adjuvants include condensation products of alkylene glycols with phenols or with organic acids, alkyl aryl sulphonates and polyoxyethylene ether or ester derivatives of alcohols or acids.

Dusts and granules may be prepared by mixing the active compound of formula (I) with an inert solid carrier. Suitable solid carriers include talc, pyrophyllite, clay, bentonite, diatomaceous earth and kaolin.

Wettable powders may be prepared by mixing the active compound with one or more solid carriers (such as those exemplified above for dusts and granules) and with one or more suitable dispersing agents, such as alkylbenzenesulphonates, polyvinyl alcohols, lignosulphonates and polyoxyalkylene glycol ethers and esters.

The concentration of the active compound of formula (I) in the composition may vary over a wide range, although it will normally be from 0.1 to 95% by weight and more preferably is from 0.5 to 70% by weight. However, the concentration is not critical and may be changed at will depending upon such factors as the form of the composition, the particular active compound chosen and its toxicity, the species of insect, arachnid or acarid to be attacked and the method of application.

The insecticidal and acaricidal compositions of the invention may also include other known insecticidal agents, such as O,O-dimethyl O-β-methyl-4-nitrophenyl) phosphorothioate, O,O-diethyl O-(2-isopropyl-4-methyl-6-pyrimidinyl) phosphorothioate or O,O-diethyl S-2-(ethylthio)ethyl phosphorodithioate; or fungicidal agents, such as kasugamycin, zinc ethylenebisdithiocarbamate or methyl benzimidazol-2-carbamate.

Thus, the invention also provides an insecticidal and/or acaricidal composition comprising at least one compound of formula (I) in admixture with a carrier or diluent.

The invention also provides a method of treating growing crops to control insects, arachnids and acarids, which comprises applying an effective amount of at least one compound of formula (I) to the crops or to the soil in which they are growing. The compound or compounds is normally applied at a concentration or aggregate concentration of at least 5 ppm for liquid preparations (i.e. liquid compositions and diluted wettable powders) and in an amount of from 7 to 150 g of active compound or compounds (I) per 10 ares for solid preparations such as dusts and granules.

The invention is further illustrated by the following Examples, of which Examples 1 to 7 illustrate the preparation of the compounds of the invention and Examples 8 to 15 illustrate their use in the control of insects and other pests.

EXAMPLE 1

O,O-di-n-propyl S-(5-methyl-3-oxo-4-isoxazolin-2-yl-methyl) phosphorodithioate (a) To a mixture of 4.95 g of 3-hydroxy-5-methylisoxazole, 1.7 g of paraformaldehyde and 20 ml of benzene were added 5 ml of thionyl chloride, and the mixture was then refluxed for 30 minutes. After completion of the reaction, the solvent and excess thionyl chloride were distilled off and diisopropyl ether was added to the brown oily residue to form crystals. Recrystallization of these crystals from diisopropyl ether gave 6.35 g (86.5% of theory) of 2-chloromethyl-5-methyl-4-isoxazolin-3-one.

(b) To a solution of 1.48 g of the 2-chloromethyl-5-methyl-4-isoxazolin-3-one thus obtained in 30 ml of acetone were added 2.52 g of crystalline potassium O,O-di-n-propyl dithiophosphate, and the resulting mixture was then stirred for 1 hour at ambient temperature. The acetone was then evaporated off and the residue was purified by column chromatography through silica gel eluted with a 20:1 by volume mixture of benzene and acetone. There were obtained 2.39 g (73.5% of theory) of O,O-di-n-propyl S-(5-methyl-3-oxo-4-isoxazolin-2-ylmethyl) phosphorodithioate, in the form of a pale yellow oil, $n^{20}_D = 1.5314$.

Elemental analysis:

Calculated for $C_{11}H_{20}NO_4PS_2$: N, 4.30%; P, 9.52%; S, 19.71%.

Found: N, 4.17%; P, 9.11%; S, 20.17%.

EXAMPLE 2

O,O-diethyl S-[1-(5-methyl-3-oxo-4-isoxazolin-2-yl)ethyl] phosphorodithioate (a) A mixture of 2.97 g of 3-hydroxy-5-methylisoxazole, 1.32 g of paraldehyde, 3 ml of thionyl chloride and 20 ml of benzene was stirred for 1 hour at 40°–50° C. On evaporating off the solvent and excess thionyl chloride, there were obtained 4.97 g of crude, crystalline 2-(1-chloroethyl)-5-methyl-4-isoxazolin-3-one.

(b) 0.81 g of the crude crystals obtained above were dissolved in 15 ml of acetone, and then 1.12 g of potassium O,O-diethyl dithiophosphate were added to the solution. The mixture was stirred for 5 minutes, and then the acetone was distilled off, leaving a residue. 10 ml of benzene were added to this residue and the mixture was then filtered and the remaining crystals were washed five times, each with 2 ml of benzene. The filtrate and the washings were combined and then concentrated, by evaporation under reduced pressure, to a volume of about 5 ml. This concentrated solution was purified by column chromatography through silica gel eluted with a 20:1 by volume mixture of benzene and acetone. There was obtained 1.03 g (66.2% of theory) of O,O-diethyl S-[1-(5-methyl-3-oxo-4-isoxazolin-2-yl)ethyl] phosphorodithioate, in the form of a yellow oil, $n^{25}_D = 1.5309$.

Elemental analysis:

Calculated for $C_{10}H_{18}NO_4PS_2$: N, 4.50%; P, 9.95%; S, 20.60%.

Found: N, 4.66%; P, 9.17%; S, 20.57%.

EXAMPLE 3

O,O-diethyl S-(4-chloro-5-methyl-3-oxo-4-isoxazolin-2-ylmethyl) phosphorodithioate (a) To a mixture of 100.2 g of 4-chloro-3-hydroxy-5-methylisoxazole, 24 g of paraformaldehyde and 400 ml of benzene were added 75 ml of thionyl chloride, whilst stirring and cooling to 10° C. The mixture was then stirred for a further 30 minutes at 10°–15° C., after which it was heated gradually over about 1 hour to reflux temperature. The solvent and excess thionyl chloride were evaporated off under reduced pressure, giving 137.5 g of crude, crystalline 4-chloro-2-chloromethyl-5-methyl-4-isoxazolin-3-one.

(b) A mixture of 0.91 g of these crude crystals, 1.20 g of potassium O,O-diethyl dithiophosphate and 15 ml of acetone was stirred for 1 hour at ambient temperature. The solvent was then distilled off and 5 ml of benzene were added to the residue. The solution was filtered and the crystalline potassium chloride filtered off was washed five times, each with 2 ml of benzene. The filtrate and the washings were combined and concentrated, by evaporation under reduced pressure, to about 5 ml. This concentrated solution was purified by column chromatography through silica gel eluted with a 10:1 by volume mixture of benzene and acetone. There were obtained 1.40 g (84.3% of theory) of O,O-diethyl S-(4-chloro-5-methyl-3-oxo-4-isoxazolin-2-ylmethyl) phosphorodithioate in the form of a pale yellow oil, $n^{20}_D = 1.5457$.

Elemental analysis:

Calculated for $C_9H_{15}ClNO_4PS_2$: N, 4.22%; Cl, 10.69%; P, 9.34%; S, 19.33%.

Found: N, 4.14%; Cl, 10.75%; P, 9.03%; S, 20.29%.

EXAMPLE 4

O,O-diethyl S-(4-chloro-5-methyl-3-oxo-4-isoxazolin-2-ylmethyl) phosphorodithioate (a) To a mixture, cooled to 10° C., of 13.4 g of 4-chloro-3-hydroxy-5-methylisoxazole, 3.3 g of paraformaldehyde and 100 ml of benzene were added, with stirring, 10 ml of thionyl chloride; the mixture was then gradually heated over about 1 hour to reach reflux. The solvent and excess thionyl chloride were then distilled off and the residue was dissolved in 50 ml of acetone to give a solution of crude 4-chloro-2-chloromethyl-5-methyl-4-isoxazolin-3-one.

(b) Meanwhile, an acetone solution of crude potassium O,O-diethyl dithiophosphate was prepared by dissolving 20 g of O,O-diethyl dithiophosphate (purity about 90%) in 100 ml of acetone and then adding, with stirring, 8 g of anhydrous potassium carbonate to the solution in small portions at ambient temperature.

(c) To the solution obtained in step (b) above was added dropwise the isoxazolinone solution obtained in step (a) above, with stirring, over a period of 5 minutes at ambient temperature. The mixture was then stirred for a further 30 minutes, also at ambient temperature. After distilling off the solvent, 100 ml of benzene and 25 ml of water were added to the residue and the benzene phase was washed, in turn, with 25 ml of a 5% w/w aqueous sodium bicarbonate solution and twice with 100 ml of a saturated aqueous sodium chloride solution. The benzene solution was then dried over anhydrous sodium sulphate and the solvent was distilled off. The residue was then purified as described in step (b) of Example 3, affording 28.5 g (85.8% of theory) of O,O-diethyl S-(4-chloro-5-methyl-3-oxo-4-isoxazolin-2-ylmethyl) phosphorodithioate, in the form of a yellow oil, $n^{20}{}_D = 1.5457$.

Elemental analysis:
Calculated for $C_9H_{15}ClNO_4PS_2$: Cl, 10.69%; N, 4.22%; P, 9.34%; S, 19.33%.
Found: Cl, 10.75%; N, 4.14%; P, 9.03%; S, 20.29%.

EXAMPLE 5

O,O-diethyl S-[α-(5-methyl-3-oxo-4-isoxazolin-2-yl)benzyl]phosphorodithioate To a solution of 1.12 g of 2-(α-chlorobenzyl)-5-methyl-4-isoxazolin-3-one in 15 ml of acetone were added 1.12 g of potassium O,O-diethyl dithiophosphate, and the mixture was then shaken for several minutes. After this, 20 ml of benzene were added to the reaction mixture and then most of the acetone was distilled off. After filtering the solution, the solvent was distilled from the filtrate and the remaining yellowish-brown oil was purified by column chromatography through silica gel eluted with a 20:1 by volume mixture of benzene and acetone. There were obtained 1.16 g (62.0% of theory) of O,O-diethyl S-[α-(5-methyl-3-oxo-4-isoxazolin-2-yl)benzyl] phosphorodithioate, in the form of a pale yellow oil, $n^{23}{}_D = 1.5697$.

Elemental analysis:
Calculated for $C_{15}H_{20}NO_4PS_2$: N, 3.75%; P, 8.29%; S, 17.17%.
Found: N, 3.77%; P, 7.54%; S, 17.51%.

EXAMPLE 6

O,O-diethyl S-[2-(5-methyl-3-oxo-4-isoxazolin-2-yl)ethyl]phosphorodithioate (a) A mixture of 10 g of 3-hydroxy-5-methylisoxazole and 56 g of 1,2-dibromoethane was refluxed for 6 hours. After cooling, the reaction mixture was subjected to column chromatography through silica gel eluted with a 3:1 by volume mixture of benzene and acetone. A yellow liquid separated, and this was crystallized with n-hexane, affording 2-(2-bromoethyl)-5-methyl-3-oxo-4-isoxazoline, melting at 39°–40° C.

(b) To a suspension of 1 g of the compound obtained in step (a) above in 20 ml of acetone were added 1.35 g of potassium O,O-diethyl dithiophosphate, and the mixture was stirred at ambient temperature and then heated for 7.5 hours at 50° C. After distilling off the acetone, diethyl ether was added to the residue and the resulting solution was washed, in turn, with a saturated aqueous solution of sodium bicarbonate and with water, and finally dried. The diethyl ether was evaporated off and the residue was purified by column chromatography through silica gel eluted with a 20:1 by volume mixture of benzene and acetone. There were obtained 1.46 g (94.2% of theory) of O,O-diethyl S[2-(5-methyl-3-oxo-4-isoxazolin-2-yl)ethyl]phosphorodithioate, $n^{23.5}{}_D = 1.5312$.

EXAMPLE 7

O,O-diethyl S-(5-methyl-3-oxo-4-isoxazolin-2-ylmethyl)phosphorothioate

To a solution of 1.48 g of 2-chloromethyl-5-methyl-4-isoxazolin-3-one in 20 ml of acetone were added 1.92 g of sodium O,O-diethyl thiophosphate, and then the mixture was stirred for 1 hour at ambient temperature. The solvent was then distilled from the reaction mixture and 50 ml of methylene chloride and 30 ml of water were added to the residue. The methylene chloride phase was separated and dried over anhydrous sodium sulphate. The solvent was then evaporated off and the residue was purified by column chromatography through silica gel eluted with a 10:1 by volume mixture of benzene and acetone. There were obtained 1.84 g (65.5% of theory) of O,O-diethyl S-(5-methyl-3-oxo-4-isoxazolin-2-ylmethyl)phosphorothioate, in the form of a pale yellow oil, $n^{26}{}_D = 1.5029$.

Following substantially the same procedures as are described in Examples 1 to 7, the following compounds were synthesized:

O,O-diethyl S-(5-methyl-3-oxo-4-isoxazolin-2-ylmethyl)phosphorodithioate: $n^{20}{}_D = 1.5450$.

O,O-diethyl S-(4-chloro-3-oxo-5-phenyl-4-isoxazolin-2-ylmethyl)phosphorodithioate; $n^{23}{}_D = 1.5984$.

O,O-diethyl S-(3-oxo-5-phenyl-4-isoxazolin-2-ylmethyl)phosphorodithioate: $n^{23}{}_D = 1.5914$; mp 38°–39° C.

O,O-dimethyl S-(5-methyl-3-oxo-4-isoxazolin-2-ylmethyl)phosphorodithioate: $n^{27}{}_D = 1.5546$.

O,O-diethyl S-(3-oxo-4-isoxazolin-2-ylmethyl)phosphorodithioate: $n^{21}{}_D = 1.5438$.

O,O-diethyl S-(3-oxobenzisoxazolin-2-ylmethyl)phosphorodithioate: $n^{23}{}_D = 1.5981$ O,O-dimethyl S-[1-(5-methyl-3-oxo-4-isoxazolin-2-yl)ethyl]phosphorodithioate; $n^{25}{}_D = 1.5407$.

O,O-dimethyl S-(3-oxobenzisoxazolin-2-ylmethyl)phosphorodithioate: $n^{25}{}_D = 1.5931$.

O,O-dimethyl S-(4-chloro-5-methyl-3-oxo-4-isoxazolin-2-ylmethyl)phosphorodithioate: $n^{22}{}_D = 1.5567$.

O,O-diisopropyl S-(4-chloro-5-methyl-3-oxo-4-isoxazolin-2-ylmethyl)phosphorodithioate: $n^{22}{}_D = 1.5292$.

O,O-dimethyl S-(4-chloro-3-oxo-5-phenyl-4-isoxazolin-2-ylmethyl)phosphorodithioate: mp 106°–107° C.

O,O-di-n-propyl S-(4-chloro-3-oxo-5-phenyl-4-isoxazolin-2-ylmethyl)phosphorodithioate: $n^{20}{}_D = 1.5838$.

O,O-diisopropyl S-(4-chloro-3-oxo-5-phenyl-4-isoxazolin-2-ylmethyl)phosphorodithioate; $n^{21}{}_D = 1.5812$.

O,O-dimethyl S-(3-oxo-5-phenyl-4-isoxazolin-2-ylmethyl)phosphorodithioate: $n^{22}{}_D = 1.6138$; mp 44°–45° C.

O,O-di-n-propyl S-(3-oxo-5-phenyl-4-isoxazolin-2-ylmethyl)phosphorodithioate: $n^{22}{}_D = 1.5802$.

O,O-diisopropyl S-(3-oxo-5-phenyl-4-isoxazolin-2-ylmethyl)phosphorodithioate: $n^{22}{}_D = 1.5760$.

O,O-diisopropyl S-(5-methyl-3-oxo-4-isoxazolin-2-ylmethyl)phosphorodithioate: $n^{20}{}_n = 1.5266$.

O,O-di-n-propyl S-(4-chloro-5-methyl-3-oxo-4-isoxazolin-2-ylmethyl)phosphorodithioate $n^{20}{}_D = 1.5336$ O,O-diethyl S-(4-bromo-5-methyl-3-oxo-4-isoxazolin-2-ylmethyl)phosphorodithioate: $n^{21}{}_D = 1.5562$.

O,O-diisopropyl S-(4-bromo-5-methyl-3-oxo-4-isoxazolin-2-ylmethyl)phosphorodithioate; $n^{21}{}_D = 1.5398$.

O,O-dimethyl S-(4-bromo-5-methyl-3-oxo-4-isoxazolin-2-ylmethyl)phosphorodithioate; $n^{22}{}_D = 1.5757$.

O,O-diethyl S-(3-oxo-5-n-propyl-4-isoxazolin-2-ylmethyl)phosphorodithioate: $n^{22}{}_D = 1.5311$.

O,O-diethyl S-(4,5-dimethyl-3-oxo-4-isoxazolin-2-ylmethyl)phosphorodithioate: $n^{20}{}_D = 1.5382$.

O,O-diisopropyl S-(4,5-dimethyl-3-oxo-4-isoxazolin-2-ylmethyl)phosphorodithioate: $n^{20}{}_D = 1.5244$.

O,O-diethyl S-[α-(3-oxo-5-phenyl-4-isoxazolin-2-yl)benzyl]phosphorodithioate: mp 99°–100° C.

O,O-diethyl S-(4-isopropyl-3-oxo-5-phenyl-4-isoxazolin-2-ylmethyl)phosphorodithioate: $n^{22}_D = 1.5689$.

O,O-di-n-propyl S-(4-isopropyl-3-oxo-5-phenyl-4-isoxazolin-2-ylmethyl)phosphorodithioate: $n^{22}_D = 1.5613$.

O,O-diethyl S-(4-chloro-5-methyl-3-oxo-4-isoxazolin-2-ylmethyl)phosphorothioate: $n^{26}_D = 1.5089$.

EXAMPLE 8

Activity against the green peach aphid

A wettable powder was prepared by homogeneously mixing and pulverizing three times in a pulverizer 10 parts of each of the test compounds indicated in Table 1, 4 parts of sodium dodecylbenzenesulphonate, 2 parts of polyvinyl alcohol and 84 parts of clay. The wettable powder thus prepared was then diluted with water to the concentration indicated in Table 1 and then 0.01% of Gramin (a spreader) was added. Using a sprayer, the diluted solution thus obtained was sprayed onto the leaves of a cabbage bearing green peach aphids (*Myzus persicae*) in an amount of 10 ml per leaf. The leaves were then placed into petri dishes and left in a room maintained at 25° C. After 20 hours, the percentage mortality of the aphids was assessed. The results are given in Table 1, which also gives the results obtained in a control experiment where the solution applied contained no active compound.

Table 1

| Test Compound No. | Mortality of aphids (%) Concentration of active compd. | | |
|---|---|---|---|
| | 100 ppm | 59 | 5 |
| 1 | 100 | 100 | 100 |
| 3 | 100 | 100 | 100 |
| 7 | 100 | 100 | 83 |
| 8 | 100 | 100 | 60 |
| 9 | 100 | 100 | 88 |
| 14 | 100 | 93 | 50 |
| 16 | 100 | 100 | 32 |
| 21 | 100 | 100 | 42 |
| 27 | 100 | 100 | 20 |
| 31 | 100 | 100 | 87 |
| 32 | 100 | 100 | 97 |
| None | 0 | | |

EXAMPLE 9

Activity against the green peach aphid

A wettable powder prepared as described in Example 8 was diluted with water to the concentration indicated in Table 2 and then poured into 30 ml bottles. Leaves of a cabbage bearing green peach aphids were placed into the bottles through the leafstalk, the mouths of the bottles were plugged with cottonwool, and the bottles were then left in a room maintained at 25° C. After 72 hours, the percentage mortality of the aphids was assessed. The results are given in Table 2.

Table 2

| Test compound No. | Mortality of aphids (%) Concentration of active compound | | | |
|---|---|---|---|---|
| | 50 ppm | 25 | 5 | 1 |
| 1 | 100 | 100 | 100 | 98 |
| 3 | 100 | 100 | 62 | 24 |
| 7 | 100 | 100 | 100 | 100 |
| 16 | 100 | 100 | 100 | 93 |
| 21 | 100 | 100 | 94 | 50 |
| None | 0 | | | |

EXAMPLE 10

Activity against the green rice leafhopper

A dust was prepared by homogeneously mixing and pulverizing twice with a pulverizer 2 parts of each in turn of the test compounds indicated in Table 3 and 98 parts of clay. A plastic pot having an inside diameter of 10.5 cm and in which 3 rice plants of height 15 cm were planted was covered by a transparent plastic cylinder having an inside diameter of 9.5 cm and a height of 25 cm. The 2% dust prepared above was then applied to the rice plants in the pot at the rate indicated in Table 3 and then about 15 final instar larvae of the green rice leafhopper (*Naphotettix cincticeps*, of the Shinwa strain, known to be resistant both to conventional organic phosphorus and carbamate insecticides) were released into each pot. After maintaining the pots for 3 days at 25° C., the percentage mortality of the larvae was assessed. The results with two repeat tests per pot, are given in Table 3.

Table 3

| Test Compound No. | Mortality of larvae (%) 2% dust amount applied per pot | |
|---|---|---|
| | 50 mg | 10 mg |
| 1 | 100 | 100 |
| 3 | 100 | 100 |
| 6 | 100 | 89.7 |
| 8 | 100 | 75.9 |
| 17 | 100 | 89.7 |
| 24 | 100 | 100 |
| 25 | 100 | 95.2 |
| 26 | 100 | 95.2 |
| 27 | 100 | 100 |
| 28 | 100 | 90.9 |
| 30 | 100 | 100 |
| 32 | 100 | 100 |
| 32 | 100 | 100 |
| 34 | 100 | 96.0 |
| None | 0 | |

EXAMPLE 11

Activity against the brown planthopper

Following substantially the same procedures as described in Example 10, the final instar larvae of the brown planthopper (*Nilaparvata lugens*) were released into pots containing rice plants dusted with a 2% dust containing the compounds shown in Table 4, and the percentage mortality of the larvae after 3 days was assessed. The results are shown in Table 4.

Table 4

| Test Compound No. | Mortality of larvae (%) 2% dust amount applied per pot | |
|---|---|---|
| | 50 mg | 10 mg |
| 1 | 100 | 79.3 |
| 7 | 100 | 85.7 |
| 8 | 100 | 25.9 |
| 24 | 100 | 33.3 |
| 26 | 100 | 13.3 |
| 27 | 100 | 56.7 |
| 30 | 100 | 36.7 |
| 31 | 100 | 40.0 |
| None | 0 | |

EXAMPLE 12

Activity against the tobacoo cutworm

Leaves of a cabbage were dipped for 30 seconds into a diluted wettable powder (prepared substantially as described in Example 8) having the concentration shown in Table 5. The leaves were then air-dried and each leaf was placed into a plastic icecream cup having a diameter of 8 cm. Third instar larvae of the tobacco cutworm (*Spodoptera litura*) were released into each cup and, beginning on the next day, there were fed untreated fresh cabbage leaves.

After 5 days, the percentage mortality of the cutworm larvae was assessed. The tests were conducted in duplicate, using 10 larvae in each test. The results are given in Table 5.

Table 5

| Test compound No. | Mortality of larvae (%) Concentration of active compound | | |
|---|---|---|---|
| | 1000 ppm | 100 | 10 |
| 1 | 90 | 10 | 0 |
| 3 | 50 | 5 | 5 |
| 7 | 100 | 55 | 0 |
| 8 | 60 | 0 | 0 |
| 9 | 45 | 30 | 5 |
| 12 | 45 | 0 | 0 |
| 14 | 90 | 20 | 0 |
| 16 | 75 | 10 | 5 |

EXAMPLE 13

Activity against the green peach aphid

Green peach aphids naturally breeding on cabbages planted on 12 October in a plastic house were sprayed on 11 January of the next year with a diluted wettable powder containing 250 ppm of the active compounds specified in Table 6, at the rate of 100 ml per plant. The number of surviving aphids was counted 3 days and 10 days after application. Two plants were used in each test. The results are shown in Table 6. The number of aphids before spraying and in the control experiment where the spray contained no active compound were rounded to the nearest ten.

Table 6

| Test compound No. | Number of surviving aphids per two plants | | |
|---|---|---|---|
| | Before spray | After 3 days | After 10 days |
| 1 | 1200 | 0 | 10 |
| 3 | 1540 | 0 | 0 |
| 7 | 1500 | 0 | 25 |
| 16 | 1630 | 0 | 0 |
| 27 | 870 | 0 | 29 |
| 31 | 1150 | 0 | 22 |
| None | 710 | 1010 | 3200 |

The aphids found on some of the plants after 10 days where there had been none after 3 days are the result of the infiltration of aphids from outside the plastic house; this indicates that, as with other known insecticides, repeated treatment of plants is necessary for complete success.

EXAMPLE 14

Activity against the two-spotted spider mite

Leaves of the cowpea (*Vigna sinensis*) bearing susceptible two-spotted spider mites (*Tetranychus urticae*) were dipped for 10 seconds into a diluted wettable powder prepared as described in Example 8, and the excess liquid was allowed to drop off. The leaves were then placed into petri dishes and the percentage mortality of bearing adult female mites was assessed after 24 hours. Furthermore, the life and death of eggs (i.e. the presence of hatching) was assessed after 14 days. The results are given in Tables 7 and 8.

Table 7

| Test compound No. | Mortality of adult female mites (%) Concentration of active compound (ppm) | | | | |
|---|---|---|---|---|---|
| | 1000 | 300 | 100 | 30 | 10 |
| 1 | 100 | 100 | 100 | 66 | 23 |
| 3 | 100 | 100 | 100 | 73 | 15 |
| 5 | 100 | 100 | 100 | 35 | 7 |
| 6 | 100 | 42 | 23 | 4 | 9 |
| None | | | 7 | | |

Table 8

| Test compound No. | Mortality of eggs (%) Concentration of active compd. (ppm) | | |
|---|---|---|---|
| | 1000 | 300 | 100 |
| 1 | 100 | 100 | 45 |
| 3 | 100 | 100 | 33 |
| None | | 3 | |

EXAMPLE 15

Activity against the comstock mealybug

Slices of a pumpkin bearing comstock mealybugs (*Pseudococcus comstocki*) were dipped for 30 seconds into a diluted wettable powder prepared as described in Example 8 to the concentration indicated in Table 9 and containing 0.02% of Gramin. The slices were then placed into petri dishes covered with filter papers. The percentage mortality of the comstock mealybugs was assessed after 1 day and after 5 days and the results are reported in Table 9.

Table 9

| Conc. | Test Compd. No. | Adult female | | | 1st to 2nd instar larvae | | |
|---|---|---|---|---|---|---|---|
| | | No. before dipping | Mortality % | | No. before dipping | Mortality % | |
| | | | 1 day | 5 days | | 1 day | 5 days |
| 500 ppm | 1 | 20 | 100 | — | 198 | 100 | — |
| | 3 | 20 | 100 | — | 236 | 100 | — |
| | 7 | 20 | 100 | — | 215 | 100 | — |
| | 16 | 20 | 100 | — | 162 | 100 | — |
| 100 ppm | 1 | 20 | 85 | 100 | 206 | 99 | 100 |
| | 3 | 20 | 90 | 100 | 210 | 99 | 99 |
| | 7 | 20 | 90 | 95 | 181 | 98 | 99 |
| | 16 | 20 | 95 | 100 | 227 | 97 | 100 |
| None | | 20 | 20 | 30 | 88 | 20 | 20 |

We claim:
1. Compounds of formula (I):

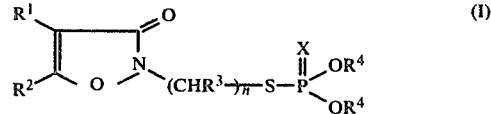

wherein:
$R^1$ represents a hydrogen atom, a lower alkyl group or a halogen atom;
$R^2$ represents a hydrogen atom, a lower alkyl group or a phenyl group;
$R^3$ represents a hydrogen atom, a lower alkyl group or a phenyl group;
$R^4$ represents a lower alkyl group;
X represents an oxygen atom or a sulphur atom; and n represents 1 or 2.

2. Compounds as claimed in claim 1, wherein:
R¹ represents a hydrogen atom, a methyl group or a halogen atom;
R² represents a hydrogen atom, a lower alkyl group or a phenyl group;
R³ represents a hydrogen atom or a methyl group;
R⁴ represents a lower alkyl group;
X represents a sulphur atom;
and n is 1.

3. An insecticidal/acaricidal composition containing (i) a carrier and (ii) an insecticidally or acaricidally effective amount of a compound of formula (I):

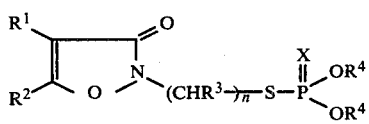

wherein:
R¹ represents a hydrogen atom, a lower alkyl group or a halogen atom;
R² represents a hydrogen atom, a lower alkyl group or a phenyl group;
R³ represents a hydrogen atom, a lower alkyl group or a phenyl group;
R⁴ represents a lower alkyl group;
X represents an oxygen atom or a sulphur atom; and n represents 1 or 2.

4. A composition as claimed in claim 3, wherein:
R¹ represents a hydrogen atom, a methyl group or a halogen atom;
R² represents a hydrogen atom, a lower alkyl group or a phenyl group;
R³ represents a hydrogen atom or a methyl group;
R⁴ represents a lower alkyl group;
X represents a sulphur atom;
and n is 1.

5. A compound according to claim 1 of the formula O,O-diethyl S-(5-methyl-3-oxo-4-isoxazolin-2-ylmethyl)phosphorodithioate.

6. A compound according to claim 1 of the formula O,O-diethyl S-(5-methyl-3-oxo-4-isoxazolin-2-ylethyl)-phosphorothioate.

7. A compound according to claim 1 of the formula O,O-diethyl S-(4-chloro-5-methyl-3-oxo-4-isoxazolin-2-ylmethyl)phosphorodithioate.

8. A compound according to claim 1 of the formula O,O-diethyl S-(4-chloro-5-methyl-3-oxo-4-isoxazolin-2-ylmethyl)-phosphorothioate.

9. A compound according to claim 1 of the formula O,O-dimethyl S-(5-methyl-3-oxo-4-isoxazolin-2-ylmethyl)phosphorodithioate.

10. A compound according to claim 1 of the formula O,O-diethyl S-(3-oxo-4-isoxazolin-2-ylmethyl)phosphorodithioate.

11. A compound according to claim 1 of the formula O,O-dimethyl S-(4-chloro-5-methyl-3-oxo-4-isoxazolin-2-ylmethyl)-phosphorodithioate.

12. A compound according to claim 1 of the formula O,O-dimethyl S-(3-oxo-5-phenyl-4-isoxazolin-2-ylmethyl)phosphorodithioate.

13. A compound according to claim 1 of the formula O,O-di-n-propyl S-(5-methyl-3-oxo-4-isoxazolin-2-ylmethyl)-phosphorodithioate.

14. A compound according to claim 1 of the formula O,O-di-n-propyl S-(4-chloro-5-methyl-3-oxo-4-isoxazolin-2-ylmethyl)phosphorodithioate.

15. A compound according to claim 1 of the formula O,O-diethyl S-(4-bromo-5-methyl-3-oxo-4-isoxazolin-2-ylmethyl)-phosphorodithioate.

16. A compound according to claim 1 of the formula O,O-dimethyl S-(4-bromo-5-methyl-3-oxo-4-isoxazolin-2-ylmethyl)-phosphorodithioate.

17. A compound according to claim 1 of the formula O,O-diethyl S-(3-oxo-5-n-propyl-4-isoxazolin-2-ylmethyl)-phosphorodithioate.

18. A compound according to claim 1 of the formula O,O-diethyl S-(4,5-dimethyl-3-oxo-4-isoxazolin-2-ylmethyl)-phosphorodithioate.

19. A compound according to claim 1 of the formula O,O-diisopropyl S-(4,5-dimethyl-3-oxo-4-isoxazolin-2-ylmethyl)-phosphorodithioate.

* * * * *

UNITED STATES PATENT AND TRADEMARK OFFICE
CERTIFICATE OF CORRECTION

PATENT NO. : 4,209,512
DATED : June 24, 1980
INVENTOR(S) : KAZUO TOMITA et al

It is certified that error appears in the above-identified patent and that said Letters Patent are hereby corrected as shown below:

Column 3, line 9: replace "dimethyl" with ---diethyl---.

Column 3, line 36, formula (II): replace "$(CHR^3)_n-V$" with ---$(CHR^3)_n-Y$---.

Column 5, line 51, formula (VIII):

$$"V-\left[\begin{array}{c}CH\\|\\R^3\end{array}\right]-V" \text{ should read } ---Y-\left[\begin{array}{c}CH\\|\\R^3\end{array}\right]_2-Y---$$

Column 10, line 52: replace "$n^{20}_n$" with ---$n^{20}_D$---.

Column 11, line 23: replace "20 hours" with ---24 hours---.

Column 12, line 36: in Table 3, under "Test Compound No.", between "30" and "32 (second occurrence), replace "32" with ---31---.

Signed and Sealed this

Ninth Day of December 1980

[SEAL]

Attest:

SIDNEY A. DIAMOND

Attesting Officer

Commissioner of Patents and Trademar